US006814698B2

(12) United States Patent
Barthel et al.

(10) Patent No.: US 6,814,698 B2
(45) Date of Patent: Nov. 9, 2004

(54) ENDOSCOPE WITH FLEXIBLE LIGHT GUIDE HAVING OFFSET DISTAL END

(75) Inventors: Thomas Clement Barthel, Becker, MN (US); Scott Allen Sundet, Edina, MN (US); Craig Louis Riedl, Long Lake, MN (US); Dinh Thuc Ha, Blaine, MN (US)

(73) Assignee: Clarus Medical, LLC, Minneapolis, MN (US)

( * ) Notice: Subject to any disclaimer, the term of this patent is extended or adjusted under 35 U.S.C. 154(b) by 0 days.

(21) Appl. No.: 09/972,812

(22) Filed: Oct. 5, 2001

(65) Prior Publication Data

US 2003/0069473 A1 Apr. 10, 2003

(51) Int. Cl.[7] ................................................ A61B 1/00
(52) U.S. Cl. ........................................ 600/139; 129/160
(58) Field of Search ................................. 600/120, 171, 600/182, 160, 139, 146, 164, 107, 144, 176, 177, 190, 199, 105, 127, 129

(56) References Cited

U.S. PATENT DOCUMENTS

| 1,915,811 A | | 6/1933 | Wolf | |
|---|---|---|---|---|
| 1,995,196 A | | 3/1935 | Wolf | |
| 2,076,741 A | | 4/1937 | Peck | |
| 2,325,831 A | | 8/1943 | Cameron | |
| 3,297,022 A | | 1/1967 | Wallace | |
| 3,677,262 A | * | 7/1972 | Zukowski | 600/120 |
| 3,918,439 A | * | 11/1975 | Zimmer | 600/104 |
| 4,086,919 A | * | 5/1978 | Bullard | 600/188 |
| 4,279,245 A | | 7/1981 | Takagi et al. | |
| 4,327,711 A | | 5/1982 | Takagi | |
| 4,349,032 A | * | 9/1982 | Koyata | 600/139 |
| 4,669,172 A | | 6/1987 | Petruzzi | |
| 4,893,613 A | * | 1/1990 | Hake | 600/152 |
| 5,003,963 A | * | 4/1991 | Bullard et al. | 600/104 |
| 5,127,393 A | | 7/1992 | McFarlin et al. | |
| 5,168,864 A | | 12/1992 | Shockey | |
| 5,183,031 A | | 2/1993 | Rossoff | |
| 5,318,008 A | * | 6/1994 | Bullard | 600/139 |
| 5,346,504 A | * | 9/1994 | Ortiz et al. | 606/192 |
| 5,394,865 A | * | 3/1995 | Salerno | 600/199 |
| 5,512,034 A | * | 4/1996 | Finn et al. | 600/138 |
| 5,580,147 A | * | 12/1996 | Salerno | 362/551 |
| 5,685,824 A | | 11/1997 | Takei | |
| 5,735,792 A | | 4/1998 | Vanden Hoek et al. | |
| 5,842,973 A | * | 12/1998 | Bullard | 600/194 |
| 5,846,183 A | | 12/1998 | Chilcoat | |
| 5,921,917 A | | 7/1999 | Barthel et al. | |
| 5,941,816 A | | 8/1999 | Barthel et al. | |
| 5,951,463 A | | 9/1999 | Lombardi et al. | |
| 6,200,306 B1 | * | 3/2001 | Klostermeyer et al. | 600/146 |
| 6,203,494 B1 | * | 3/2001 | Moriyama | 600/144 |
| 6,402,687 B1 | * | 6/2002 | Ouchi | 600/139 |

* cited by examiner

*Primary Examiner*—Beverly M. Flanagan
(74) *Attorney, Agent, or Firm*—Olson & Hierl, Ltd.

(57) ABSTRACT

An optical fiber viewing assembly for an endoscope has a light guide with an elastically flexible portion and a substantially rigid pre-curved distal portion. The viewing assembly is particularly suited for traversing bends of relatively small radii in an endotracheal breathing tube without scraping accumulated biological material from the inner surface of the breathing tube that could collect on the distal end of the light guide and obscure the endoscopic view.

19 Claims, 2 Drawing Sheets

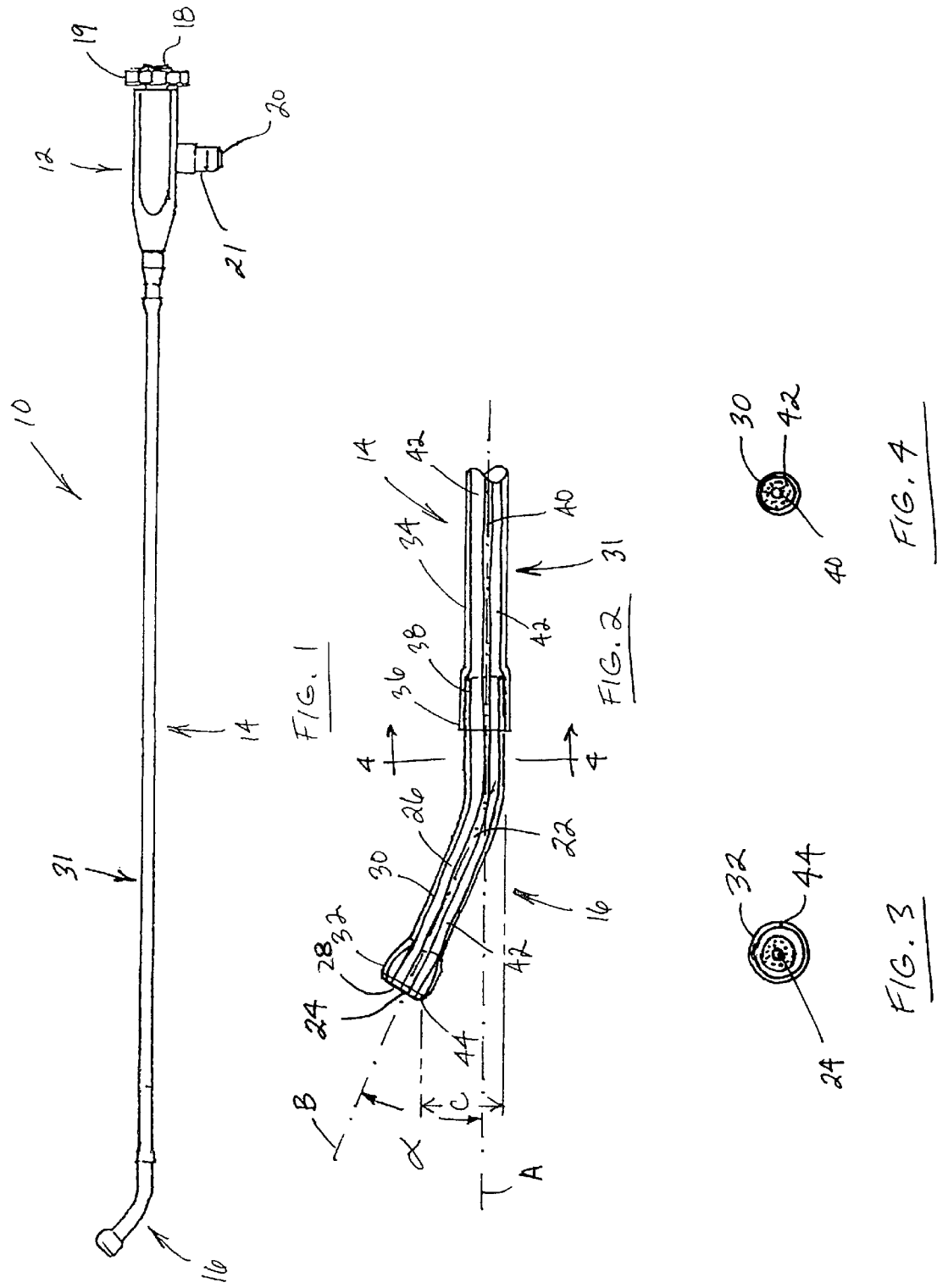

ENDOSCOPE WITH FLEXIBLE LIGHT GUIDE HAVING OFFSET DISTAL END

TECHNICAL FIELD OF THE INVENTION

This invention relates generally to endoscopes, and more particularly to endoscopes useful in connection with placing or confirming placement of endotracheal breathing tubes.

BACKGROUND OF THE INVENTION

Endotracheal intubation is a common medical procedure by which a flexible plastic endotracheal breathing tube is inserted into a patient's trachea for providing oxygen or anesthetic gases to the lungs. Usually, the endotracheal tube is introduced into the patient's trachea after the patient has been sedated or has become unconscious. The endotracheal tube must be inserted past the patient's teeth and tongue and further past the epiglottis and vocal cords into the trachea. When so placed, the endotracheal tube is disposed in a curved configuration that may have a relatively small radius of curvature on the order of about two inches.

Initial placement of the endotracheal breathing tube is often performed under emergency conditions. Therefore, it is desirable to inspect, and if necessary change, a patient's endotracheal tube soon after the patient arrives at the emergency room of the hospital. In cases of long-term intubation, the breathing tube also should be inspected at weekly intervals or whenever the patient is moved with a change of personnel responsible for the patient's care. This is to avoid or alleviate harmful reactions from long-term intubation such as granulation tissue reaction, infection, and stenosis of the trachea, larynx or subglottis, and to confirm continued proper placement.

An endoscope can be used by the practitioner to view the patient's tracheal area and more accurately place or assess the placement of the breathing tube. Such a device also can be used by the practitioner to verify proper placement of the breathing tube immediately after intubation or at any time thereafter.

Many types of endoscopes use a light guide having a fiber optic bundle that cooperates with an eyepiece optical assembly to permit viewing within a body cavity. The fiber optic bundle and any associated connectors generally can be referred to as a viewing assembly. The fiber optic bundle can include an image bundle and at least one illumination bundle. The image bundle is a coherent bundle of image-carrying optical fibers. The illumination bundle is a bundle of illumination light-carrying optical fibers.

The image bundle typically cooperates with the eyepiece optics, and the illumination bundle typically cooperates with a light source. The distal ends of the image bundle and the illumination bundle are often co-terminal at the distal end of the light guide. The proximal end of the image bundle may terminate in a connector that cooperates with the eyepiece. The proximal end of the illumination bundle may terminate in a connector that cooperates with the light source. The illumination bundle carries light from a light source to the distal end of the light guide to illuminate the area in front of the endoscope. An image of the illuminated area is then carried back through the light guide to the eyepiece via the image bundle.

Many endoscopes also include a handle that holds the eyepiece and the light guide and associated connectors. Some hand held endoscopes include a power source and a light source associated with the handle. Also, the handle can be configured to connect to the light guide and to the eyepiece to hold the entire system in operable relationship. The eyepiece assembly of an endoscope can be used with the naked eye of the practitioner or, alternatively, can be configured to connect to a camera or an electronic monitor to provide still photographs or video images.

Some intubation endoscopes are provided with a slender, elongate light guide that is plastically and inelastically malleable. In other words, the light guide can be bent or curved from its ordinarily straight configuration and will hold the desired configuration without springing back to the original straight configuration. This can be achieved by encasing the light guide with a thin-walled tube made of steel, aluminum or other plastically and inelastically malleable material. Other malleable, biocompatible metals and materials would also be suitable. The practitioner can pre-shape the light guide to a desired curvature to fit the curvature of the breathing tube and the patient's anatomy. The pre-shaped light guide can be placed within and inserted along with the breathing tube so that the practitioner can view anatomic structures as the tube is inserted into the patient.

In cases where a breathing tube has been placed previously, it is desirable to visually inspect the placement of the breathing tube. When inspecting a previously placed breathing tube, use of an endoscope having a plastically and inelastically malleable light guide has some disadvantages. The light guides of such endoscopes are usually too stiff to easily traverse the bend of the breathing tube while being pushed from the outside. Such bends are often curved to relatively small radii of curvature. An endoscope having an elastically flexible light guide that can bend to relatively small radii without excessive resistance to flexure is more suitable for inspecting previously placed breathing tubes.

As an elastically flexible light guide is inserted into a previously placed breathing tube, the distal end of the light guide can follow the inner wall of the curved breathing tube along the outer radius of the bend. Lateral forces imposed on the distal end of the light guide by the wall of the breathing tube cause the flexible light guide to bend, generally following the curvature of the breathing tube. Consequently, the light guide can traverse the full length of the breathing tube while being pushed from an external location.

If the breathing tube has been in place for some time, inspection with a flexible endoscope can be complicated by mucus and fluids that may have accumulated on the interior surface of the breathing tube. As the endoscope light guide is inserted into the endotracheal breathing tube, the distal objective end of the light guide tends to contact the inner wall of the tube as the light guide passes through the bend in the breathing tube. As a result, mucus and other deposits on the inner wall of the breathing tube may incidentally be scraped from the inner wall of the tube and become accumulated on the distal end of the light guide, obscuring the endoscopic view.

In a flexible light guide undergoing curvature from contact with the inner wall of the breathing tube, the curvature tends to occur somewhat proximally of the distal end, with the most terminal portion of the light guide tending to remain straight. Therefore, the distal end would approach the curved inner wall of the breathing tube at an angle and would tend to dig into the inner wall of the breathing tube, which would aggravate the problem of scraping up mucus or other fluids that could obscure the view. Moreover, the angular approach may cause the distal end to stick to the breathing tube wall rather than slide freely along the tube wall, thereby impeding insertion.

It would be advantageous to provide an endoscope having an elastically flexible light guide that can more readily follow small radius bends of a breathing tube while avoiding accumulation of biological material on the terminal end of the optics. This and other advantages are provided by the present invention.

SUMMARY OF THE INVENTION

The present invention involves a viewing assembly for an endoscope particularly well adapted for inspecting an endotracheal breathing tube in an intubated patient. A viewing assembly of the present invention can be inserted into a curved endotracheal tube and pushed through the curved portion while substantially avoiding scraping accumulated biological material from the wall of the breathing tube. This alleviates the problem of scraped up material collecting on the distal end of the viewing assembly and obscuring the endoscopic view.

According to one aspect of the present invention, an endoscope includes an elongate viewing assembly having a flexible main portion bendable between a relaxed configuration and a strained configuration. The viewing assembly also has a distal portion connected to the main portion and having a distal end that is offset laterally such as by being angled or bent with respect to the main portion. The distal portion is preferably made of a rigid metal material or a rigid preformed or heat-formed polymeric material.

According to another aspect of the present invention, an endoscope includes an elongate viewing assembly having a flexible main portion bendable between a relaxed configuration and a strained configuration. The viewing assembly also has a substantially rigid distal portion connected to the main portion and disposed at an acute angle relative to the main portion. The angle is preferably in the range of about 3 degrees to about 30 degrees.

A further aspect of the present invention involves an endoscope including a handle, a light source, an optical eyepiece, and a viewing assembly. The viewing assembly includes an elongate member comprising a light guide operably connectable to the handle, light source and optical eyepiece. The light guide has a flexible main portion bendable between a relaxed configuration and a strained configuration, and a substantially rigid distal portion connected to the main portion and having a distal end offset laterally from the main portion.

Yet another aspect of the present invention involves a method of viewing a curved endotracheal tube in an intubated patient. The method includes the step of providing an endoscope with an elongate light guide having a flexible main portion and a distal portion having a distal end laterally offset from the flexible portion. A further step involves inserting the light guide into the endotracheal tube with the distal end offset in the direction of curvature of the endotracheal tube. Another step includes advancing the light guide within the endotracheal tube.

BRIEF DESCRIPTION OF THE DRAWINGS

In the drawings,

FIG. 1 is a side view of a viewing probe of the present invention;

FIG. 2 is an enlarged longitudinal cross-sectional view of a portion of the viewing assembly of FIG. 1;

FIG. 3 is an axial end view of the distal portion of the viewing assembly of FIG. 1;

FIG. 4 is a cross-sectional view of the distal portion of the viewing assembly of FIG. 1, taken in plane 4—4 of FIG. 2 and viewed in the direction of the arrows.

DESCRIPTION OF THE PREFERRED EMBODIMENT

Figure 5:
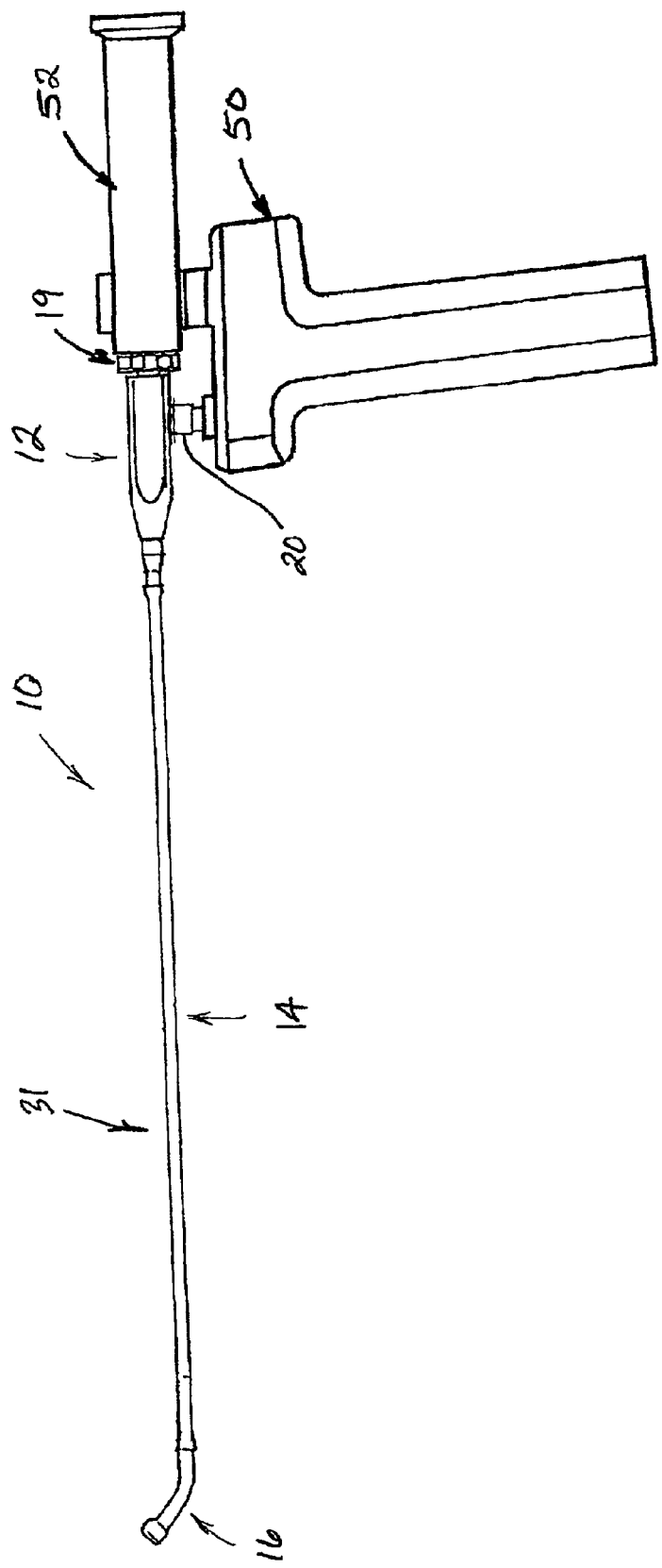
FIG. 5 is a side assembly view of an endoscope system including the viewing assembly of FIG. 1.

FIGS. 1–4 show a viewing assembly 10 comprising a portion of an endoscope system that is particularly useful in connection with a patient who has been intubated with an endotracheal breathing tube having a typical inside diameter up to about 8 mm. Viewing assembly 10 includes a proximal body 12 and a light guide 14 having a distal portion 16. Light guide 14 preferably has a length in the range of about 12 inches to about 22 inches. A length of about 15 inches to about 16 inches is more preferred. Distal portion 16 preferably has a diameter of about 0.13 inch. Proximal body 12 includes a first optical port 18 and connector 19 for attachment to imaging optics, and a second optical port 20 and connector 21 for attachment to a light source. As shown, a central imaging optical fiber bundle 22 extends from first optical port 18 through light guide 14 to distal portion 16. Light from the object to be viewed is gathered at the distal objective end 24 of the central imaging optical fiber bundle 22 and conveyed therethrough to the imaging optics via the first optical port 18. A peripheral illumination optical fiber bundle 26 surrounds the central imaging optical fiber bundle 22 and extends from second optical port 20 through light guide 14 to distal portion 16. Light from the light source enters second optical port 20 and is conveyed by the peripheral illumination optical fiber bundle 26 to distal portion 16 where the light exits from the distal end 28 of the illumination optical fiber bundle 26 to illuminate the object to be viewed.

Light guide 14 includes a flexible main portion 31 disposed between and connected to proximal body 12 and distal end 16. Main portion 31 includes a flexible, thin-walled sheath 34, preferably constructed of biocompatible polymeric material. Distal portion 16 includes a proximal end 38 that is axially aligned with and extends axially from the distal end 36 of main portion 31 along axis A. Distal portion 16 further includes a distal end 44 that is laterally offset from axis A and hence from main portion 31. As shown, the offset of distal end 44 relative to main portion 31 is provided by distal portion 16 being bent or pre-curved to have a rest or relaxed orientation in which the distal end 44 has an axis B that diverges distally at an acute angle relative to axis A of main portion 31.

Referring especially to the embodiment of FIGS. 2–4, distal portion 16 preferably includes a thin-walled, relatively stiff tube 30 having a radiused tip 32. The distal portion is preferably substantially rigid, but can be made of a flexible or resilient material that has a rest orientation such that the distal portion is offset from the main portion.

As shown in FIGS. 2–4, tip 32 can comprise a ball shape and can be enlarged relative to tube 30. Alternatively, tip 32 can have the same or a similar diameter as that of tube 30. Preferably, tip 32 has a diameter of about 0.20 inch. Tube 30 is preferably constructed of biocompatible stainless steel, other metal, or polymeric material, and has a length of about 0.5 to about 1.5 inches. Tube 30 has a proximal end 38 and a distal end 44. The longitudinal axis of tube 30 traverses a bend between proximal end 38 and distal end 44 at an acute angle α. At its proximal end 38, tube 30 is axially aligned with and connected to the distal end 36 of sheath 34 of light guide 14. Tube 30 is preferably bent to have an axis B at distal end 44 that diverges distally at an acute angle relative to the axis A at the proximal end 38. The acute angle between axes A and B is α, Preferably, the acute angle α is in the range of about 3 degrees to about 30 degrees, more preferably in the range of about 10 degrees to about 25 degrees or about 15 degrees to about 30 degrees, and even more preferably in the range of about 15 degrees to about 25 degrees. An angle α of about 20 degrees is most preferred. Tip 32 is offset laterally from the proximal end 38 of distal portion 16 by an offset distance C. Distance C is preferably at least about 1 mm and less than about 5 mm, and more preferably about 2 mm to about 3 mm.

The distal end 36 of sheath 34 is fitted over and secured to the proximal end 38 of tube 30, such as by adhesive. Disposed within distal portion 16 and sheath 31 of light guide 14 and extending therethrough is a central imaging optical fiber bundle 22 surrounded by an illumination optical fiber bundle 26, the purposes of which were described above.

Main portion 31 and distal portion 16 preferably are constructed of dissimilar materials, the sheath 34 preferably comprising a polymeric material and the tube 30 preferably comprising a metal material. Alternatively, sheath 34 and tube 30 can be comprised of substantially similar materials, i.e., polymeric materials, while having different flexibilities. For example, sheath 34 and tube 30 could be constructed integrally of the same polymeric material, with the difference in flexibility being provided by differences in wall thickness or special treatment of the material comprising distal portion 16 to increase its stiffness relative to main portion 31. As another alternative, the stiffness of distal portion 16 could be increased by way of an internal sleeve fitted therein to provide the desired angle.

Main portion 31, comprised of sheath 34 and fiber optic bundles 22 and 26 disposed therein, is flexible and elastic and of relatively low stiffness or rigidity. Main portion 31 is bendable between a relaxed configuration and a strained configuration. Even if bent to a strained configuration in which the radius of curvature is less than about two inches, main portion 31 preferably will rebound elastically substantially to the relaxed configuration. Main portion 31 preferably will not incur a substantial permanent deformation when bent to the strained configuration. In the relaxed configuration, the radius of curvature is preferably at least about 4 inches, and more preferably main portion 31 is substantially straight.

Main portion 31 of light guide 14 is flexible as demonstrated by the relatively small radius to which it can be bent or curved, and elastic as demonstrated by the rebound differential in radius of curvature between the strained configuration and the relaxed configuration. Main portion 31 has a flexural rigidity, defined as the product of its moment of inertia, I, and its tension modulus of elasticity, E. The flexural rigidity, IE, is relatively low. In contrast, the distal portion 16 is relatively stiff, or rigid, to substantially maintain the pre-formed angular bend under the forces normally encountered during use of the viewing assembly 10. The flexural rigidity of distal portion 16 is relatively large.

The flexibility, elasticity, and relatively low rigidity of main portion 31 works in concert with rigidly pre-curved or offset distal portion 16 to provide particular advantages and improved performance over prior art endoscopes for use in the field of endotracheal intubation. For example, the flexibility and relatively low stiffness, or low flexural rigidity, of main portion 31 provides for the endoscope to be pushed through an emplaced breathing tube and traverse bends of relatively small radii. The elasticity of light guide 14 provides that light guide 14 will spring back after traversing a bend, preferably at least about halfway to the relaxed orientation. More preferably, the light guide 14 will not acquire a substantial permanent set or deformation. This is advantageous if the endoscope must traverse a subsequent bend of opposite direction, and if the endoscope is to be reused with another patient after being sterilized.

The distal portion 16 is advantageously pre-bent or pre-curved through an acute angle α in the range of 3 to 30 degrees, most preferably about 20 degrees, and is sufficiently stiff or flexurally rigid to substantially maintain the preselected acute angle. This provides the advantage of an endoscope in which the angle of view is preferably at an acute angle relative to the principal longitudinal axis of the endoscope, thereby affording a wider field of view as the endoscope is rotated through 360 degrees about its longitudinal axis. The pre-curved distal portion 16 also allows the light guide 14 to more easily follow the curvature of the endotracheal breathing tube. This can be accomplished by rotating the endoscope so that the distal portion 16 is curved in the direction of curvature of the breathing tube prior to advancing the lightguide 14 through the breathing tube. Yet another advantage of the pre-curved or bent distal portion 16 is that the terminus of the light guide 14 can be kept from scraping along the inner wall of the breathing tube by steering the endoscope as described above for traversing bends in the breathing tube. The pre-curved distal portion 16 provides for the distal tip 32 to be laterally offset from main portion 31. This offset can be used to advantage to alleviate the problem of the distal end scraping up deposits on the inner wall of the breathing tube by keeping the distal tip 32 substantially displaced from the inner wall as the light guide 14 is advanced through the breathing tube. Without the offset, such deposits might collect on the objective end of light guide 14 and obscure or distort the view through the imaging fiber optic bundle.

Proximal body 12 and first and second optical ports 18 and 20, as well as associated viewing optics, light source and handle are described in U.S. Pat. No. 5,951,463, to Lombardi et al., which description is hereby incorporated by reference. The preferred embodiment of viewing assembly 10 differs from that illustrated and described in the above-referenced patent with respect to the configuration and characteristics of the light guide 14 and distal portion 16, which were described in detail above.

FIG. 5 shows the viewing assembly 10 in combination with handle and light source 50 and viewing optics 52, both of which are described in U.S. Pat. No. 5,951,463, incorporated by reference.

Although the present invention has been described in detail in terms of a preferred embodiment, no limitation on the scope of the invention is intended.

We claim:

1. An elongate viewing assembly for use as part of an endoscope, comprising:
    a) a flexible main portion bendable between a relaxed configuration and a strained configuration as the viewing assembly is guided through a lumen and carrying an imaging optical fiber and an illumination optical fiber; and
    b) a substantially fixedly rigid distal portion connected to the main portion and having a pre-curved rest orientation and a distal end that is offset laterally from the main portion.

2. The viewing assembly of claim 1, wherein the distal portion is substantially rigid.

3. The viewing assembly of claim 1, wherein the offset of the distal end is in the range of about 1 millimeter to about 5 millimeters.

4. The viewing assembly of claim 1, wherein the distal portion has a diameter in the range of about 2 millimeters to about 5 millimeters.

5. The viewing assembly of claim 1, wherein the distal portion has a proximal end, the proximal end having an axis axially aligned with the main portion and the distal end having an axis diverging distally at an acute angle relative to the axis of the proximal end.

6. The viewing assembly of claim 1, wherein the main portion and distal portion comprise substantially dissimilar materials.

7. The viewing assembly of claim 1, wherein the main portion and distal portion comprise substantially similar materials.

8. The viewing assembly of claim 1, wherein the main portion includes a sheath comprising polymeric material.

9. The viewing assembly of claim 1, wherein the distal portion includes a tube comprising metal material.

10. The viewing assembly of claim 1, wherein the main portion and distal portion are integrally constructed.

11. A viewing assembly for use as part of an endoscope, comprising:
  a) a flexible portion that is bendable between a relaxed configuration having a radius of curvature no less than about four inches and a strained configuration having a radius of curvature less than about two inches, and that rebounds elastically from the strained configuration at least about halfway to the relaxed configuration; and
  b) a distal portion pre-curved in a relaxed configuration and traversing a bend in the range of about 3 degrees to about 30 degrees.

12. The viewing assembly of claim 11 wherein the distal portion is substantially rigid.

13. The viewing assembly of claim 11, wherein the substantially rigid portion traverses a bend in the range of about 10 degrees to about 25 degrees.

14. The viewing assembly of claim 11, wherein the substantially rigid portion traverses a bend in the range of about 15 degrees to about 11 degrees.

15. The viewing assembly of claim 14, wherein the substantially rigid portion traverses a bend in the range of about 15 degrees to about 25 degrees.

16. The viewing assembly of claim 14, wherein the substantially rigid portion traverses a bend of about 20 degrees.

17. An endoscope comprising:
  a handle;
  a light source;
  an optical eyepiece; and
  a viewing assembly including an elongate member operably connectable to the handle, light source and optical eyepiece, and having a flexible main portion bendable between a relaxed configuration and a strained configuration as the viewing assembly is guided through a lumen, and a substantially fixedly rigid distal portion connected to the main portion and having a distal end offset laterally from the main portion and a distal tip having a diameter greater than that of the distal portion.

18. The endoscope of claim 17, wherein the offset of the distal end is in the range of about 1 millimeter to about 5 millimeters.

19. The endoscope of claim 17, wherein the distal portion has a diameter in the range of about 2 millimeters to about 5 millimeters.

* * * * *

UNITED STATES PATENT AND TRADEMARK OFFICE
CERTIFICATE OF CORRECTION

PATENT NO.    : 6,814,698 B2
DATED         : November 9, 2004
INVENTOR(S)   : Thomas Clement Barthel et al.

It is certified that error appears in the above-identified patent and that said Letters Patent is hereby corrected as shown below:

Column 4,
Line 40, delete "end 36" and insert -- end 38 --.

Column 8,
Line 6, delete "11 degrees" and insert -- 30 degrees --.

Signed and Sealed this

First Day of November, 2005

JON W. DUDAS
*Director of the United States Patent and Trademark Office*